United States Patent [19]

Bombardelli

[11] Patent Number: 6,080,739
[45] Date of Patent: Jun. 27, 2000

[54] COLCHICINE-SKELETON COMPOUNDS, THEIR USE AS MEDICAMENTS AND COMPOSITIONS CONTAINING THEM

[75] Inventor: Ezio Bombardelli, Milan, Italy

[73] Assignee: Indena S.p.A., Milan, Italy

[21] Appl. No.: 09/180,875

[22] PCT Filed: May 21, 1997

[86] PCT No.: PCT/EP97/02577

§ 371 Date: Nov. 24, 1998

§ 102(e) Date: Nov. 24, 1998

[87] PCT Pub. No.: WO94/47577

PCT Pub. Date: Dec. 18, 1997

[30] Foreign Application Priority Data

Jun. 7, 1996 [IT] Italy ................................ MI96A1168

[51] Int. Cl.[7] ........................ A61K 31/12; A61K 31/536; C07C 49/755; C07D 265/34
[52] U.S. Cl. ........................ 514/229.5; 514/546; 514/548; 514/680; 544/99; 560/194; 560/255; 568/43; 568/326
[58] Field of Search ................ 544/99; 560/194, 560/255; 568/43, 326; 514/229.5, 546, 548, 680

[56] References Cited

U.S. PATENT DOCUMENTS 3,442,953  5/1969  Muller et al. ........................ 260/590
4,349,548  9/1982  Jones ................................. 424/248.4

FOREIGN PATENT DOCUMENTS 2 019  9/1963  France .
3 032  12/1964  France .

OTHER PUBLICATIONS

Al–Tel et al., "New Natural Colchicinoids: Indications of Two Possible Catabolic Routes for the Colchicine Alkaloids", *J. Nat. Prod.*, vol. 53, No. 33, 623–629 (1990).

Banwell et al., "Semisyntheses, X–Ray Crystal Structures and Tubulin–Binding Properties of 7–Oxodeacetamidocolchicine and 7–Oxodeacetamidoisocolichicine", *Aust. J. Chem.*, vol. 45, 1577–1588 (1992).

Shi et al., "Antitumor Agents. 172. Synthesis and Biological Evaluation of Novel Deacetamidothiocolchicin–7–ols and Ester Analogs as Antitubulin Agents", *J. Med. Chem.*, vol. 40, 961–966 (1997).

*Primary Examiner*—Richard L. Raymond
*Attorney, Agent, or Firm*—Pennie & Edmonds LLP

[57] ABSTRACT

The present invention relates to colchicine and thiocolchicine derivatives which can be obtained from these molecules by functionalization of the C-7 to ketone or functionalization of the amino group. Said compounds have a marked antiblastic activity both on the normal cancer cells and on the chemoresistant phenotype. The compounds of the invention can be administered both by injection and orally.

13 Claims, No Drawings

COLCHICINE-SKELETON COMPOUNDS, THEIR USE AS MEDICAMENTS AND COMPOSITIONS CONTAINING THEM

This application is a 371 of PCT/EP97/02577, filed May 21, 1997.

TECHNOLOGICAL BACKGROUND

The present invention relates to novel colchicine derivatives having antiproliferative, antineoplastic and antiinflammatory activities, the methods for the preparation thereof and the pharmaceutical formulations containing them.

Colchicine is a known pseudo-alkaloid widely used for a very long time in therapy for the treatment of gout, a pathology on which it acts very quickly and specifically, even though it should be used for short times due to its toxicity. A colchicine derivative, namely thiocolchicoside, is widely used to treat contractures and in inflammatory conditions on skeletal muscles. In addition, colchicine is a very potent antiblastic agent, which acts blocking the formation of the mitotic spindle during cell division; this latter aspect has been investigated thoroughly for any antineoplastic activity and a great deal of colchicine derivatives have been prepared to this purpose. Colchicine as such and a number of its derivatives could not be used clinically due to their high toxicity, and therefore their unacceptable risk/benefit ratio. Only one colchicine derivative, demecoicine, is used in some degree in oncology for the treatment of some leukemia forms.

Therefore the problem exist of the availability of antineoplastic medicaments having a satisfactory risk/benefit ratio, i.e. a high therapeutic activity with poor or no side-effects.

Another problem in the antineoplastic field is the resistance to the medicament which takes place in specific phenotypes.

Now it has surprisingly been found that some colchicine derivatives have a high cytotoxic activity both on the normal cancerous cells and on the corresponding resistant phenotype (MDR).

The compounds of the invention are potent apoptosis inducers, proving to be markedly better than the compounds of the prior art. Due to their lipophilic, characteristics, the compounds are particularly bioavailable after oral administration. Moreover, the compounds of the present invention can be administered by the parenteral or topical routes as well.

SUMMARY OF THE INVENTION

The present invention relates to compounds of formula (I)

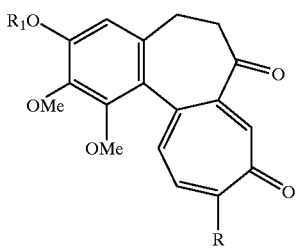

(I)

wherein R is a methoxy or methylthio group and $R_1$ is a straight or branched alkyl or alkenyl group having 1 to 6 carbon atoms, or an alicyclic or heterocyclic moiety, a saturated or unsaturated mono or dicarboxylic or amino acidic acyl residue or a β-D-glucose or 6-deoxygalactose residue.

Examples of alkyl group are methyl, ethyl, propyl, isopropyl, n-butyl, iso-butyl, t-butyl, pentyl, neopentyl, hexyl.

Examples of alkenyl group are propenyl, 1-butenyl, 2-butenyl, 1-pentenyl.

Examples of alicyclic group are cyclopropyl, cyclobutyl, cyclopentyl, cyclohexyl.

Examples of heterocyclic group are benzotriazolyl, methyltetrazolyl.

Examples of acyl residue are ximenoyl, succinyl, aspartyl.

DETAILED DESCRIPTION OF THE INVENTION

The compounds of formula I are prepared starting from the natural compounds colchicine or thiocolchicine or from the C3-derivatives thereof commercially available or obtainable with methods known in literature. As described in literature, the C3 derivatives can be prepared by reacting the 3-O-dimethyl derivative with an alkyl or acyl halide. The hydrolysis of said compounds with strong mineral acid aqueous solutions allows to obtain selectively, changing the temperature and the reaction time, the corresponding N-deacetyl derivatives. In particular, the deacetylation of thiocolchicine or of the C3 derivatives thereof can be carried out by subjecting the compounds to acidic hydrolysis; in the case of thiocolchicine, the hydrolysis with halo acids or, more preferably, with sulfuric acid (20% $H_2SO_4$—120 h), allows one to obtain N-deacetylthiocolchicine and 3-demethyl-N-deacetylthiocolchicine in nearly quantitative yields.

The N-deacetyl derivatives are reacted with 4-formyl-1-methylpyridinium-p-toluenesulfonate and 1,8-diazabicyclo [5.4.0]undec-7-ene (DBU) to prepare the compounds of formula I.

Alternatively, reacting the N-deacetyl derivatives with 2,3-ditert-butyl-1,2-benzoquinone, the compounds of formula II are obtained:

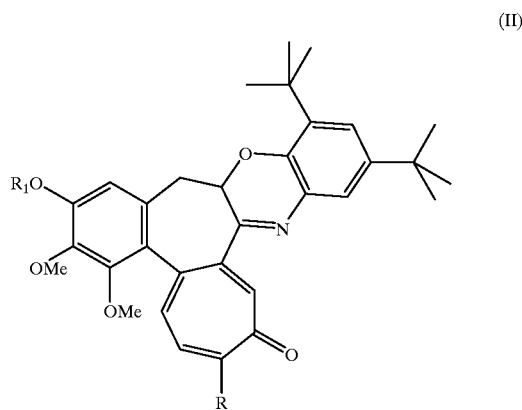

(II)

wherein R and $R_1$ have the meanings described above.

A further embodiment of the present invention encompasses the compounds of formula II.

The compounds of the invention exhibit a remarkable antineoplastic activity both in vitro and in vivo.

The table shows the antimitotic activity of the compounds of the invention on cultured breast tumour explants normal (MCF-7) or resistant to both adriamycin and vinblastin (MCF7-ADR), compared with colchicine and taxol.

TABLE

| Compounds | IC₅₀ (nM) | | |
|---|---|---|---|
| | MCF7-ADR | MCF-7 | MCF7-ADR/MCF7 |
| Colchicine | 12,000 | 1.8 | 6,600 |
| Compound Ia | 15 | 6.2 | 2.4 |
| Compound Ib | 40 | 23 | 1.7 |
| Compound IIa | 52 | 17 | 3.0 |
| Taxol | 2,400 | 2.3 | 1,043 |

This table evidences that the compounds of the invention have significant advantages on the resistant cell lines, which are nowadays considered the main target of cytotoxic medicaments.

Moreover, the compounds according to the present invention have antiinflammatory and antiarthritis activities (degenerative rheumatoid arthritis and similar pathologies) and they can be incorporated in pharmaceutical formulations useful for the administration of the medicament for the indicated pathology. Formulations for intravenous, oral, transdermal, epicutaneous administrations can conveniently be prepared.

Among the excipients useful to prepare said formulations, natural and synthetic phospholipids proved to be particularly useful for preparing liposomial forms for the parenteral and/or topical routes. The same formulations proved to be useful in the topical treatment of cutaneous epitheliomas and in cutaneous hyperproliferative conditions, such as psoriasis. In the specific antineoplastic field, besides the phospholipids which allow the administration of the medicament in the liposomial form, some surfactants such as polyethoxylated castor oils or polysorbates acting synergistically with the active ingredient, turned out to be particularly useful. Preferably the active principle is micronized to dissolve the compound in water. A surprisingly active, convenient form is the complex of these compounds with cyclodextrins.

In oncology, the products are used at dosages from 1 to 100 mg/m².

EXAMPLES

The following examples further illustrate the invention.

Example 1

Preparation of Thiocolchicone from N-deacetylthiocolchicine (Ia: R=SMe; R₁=Me)

100 ml of $CH_2Cl_2$ and 30 ml of DMF are mixed under nitrogen atmosphere, then 4 g of deacetylthiocolchicine (M.W. 373, 10.7 mmol) and 24.2 g of 4-formyl-1-methylpyridinium p-toluenesulfonate (M.W. 279, 15 mmol) are added; the whole is refluxed for 3 hours or until the amine disappears. The solution is cooled to 0° C. and then added with 1.94 g of DBU (M.W. 152, 12.8 mmol), drop by drop, to obtain a dark red solution. After 15 minutes, 150 ml of an oxalic acid aqueous solution are added, the mixture is left to react overnight, then repeatedly extracted with $CH_2Cl_2$; dried over sodium sulfate and the solvent is evaporated off to dryness. The residue is crystallized from ethyl acetate to obtain a 78% yield. Thiocolchicone has the following chemical-physical and spectroscopical characteristics.

M.p. 212° C.

MS (E.I.): 372 m/z (35%)-344 (55%)-329 (6%)-311 (13%)-301 (4%)-287 (8%)-267 (4%)-243 (4%)-215 (4%)-84 (64%)-49 (100%). ¹H-NMR (300 MHz, $CDCl_3$)

| ppm | molt | int | type | J(Hz) | J(Hz) | J(Hz) |
|---|---|---|---|---|---|---|
| 2.45 | s | 3H | SME | | | |
| 2.68 | ddd | 1H | H-5eq. | 13.4 | 4.8 | 1.9 |
| 2.81 | ddd | 1H | H-6ax | 16.6 | 13.4 | 4.8 |
| 2.95 | ddd | 1H | H-6eq | 16.6 | 5.5 | 1.9 |
| 3.11 | ddd=td | 1H | H-5ax | 13.1 | 13.5 | 5.6 |
| 3.57 | s | 3H | OMe | | | |
| 3.88 | s | 3H | OMe | | | |
| 3.90 | s | 3H | OMe | | | |
| 6.56 | s | 1H | H-4 | | | |
| 6.96 | s | 1H | H-8 | | | |
| 7.07 | AB | 1H | H-11 | 10.2 | | |
| 7.27 | AB | 1H | H-12 | 10.2 | | |

¹³C-NMR (300 MHz, $CDCl_3$): 15.8 ppm (SMe)-30.0 (C-5)-48.0 (C-6)-56.7 (OMe-3)-61.8 (OMe-2)-61.8 (OMe-1)-107.8 (C-4)-125.3 (C-12)-127.0 (C-11)-130.7 (C-8)-134.4 (C-4a)-136.1 (C-12a)-136.5 (C-12)-142.3 (C-2)-150.4 (C-1)-152.6 (C-7a)-154.6 (C-3)-160.7 (C-10)-182.9 (C-9)-206.2 (C-7).

Example 2

Preparation of Colchicone from N-deacetyl-colchicine (Ib: R=OMe; R₁=Me)

3.58 g of N-deacetylcolchicine are treated according to the procedure of Example 1. 2.6 g of colchicone are obtained, having the following chemical-physical and spectroscopical characteristics.

MS (E.I.): 356 m/z (100%)-328 (95%)-313 (25%)-300 (22%)-285 (18%)-271 (26%)-253 (13%)-238 (8%)-227 (13%)-199 (16%)-171 (11%). ¹H-NMR (300 MHz, $CDCl_3$).

| ppm | molt | int | type | J(Hz) | J(Hz) | J(Hz) |
|---|---|---|---|---|---|---|
| 2.67 | ddd | 1H | H-5β | 13.7 | 5.0 | 2.2 |
| 2.82 | ddd | 1H | H-6β | 16.6 | 13.6 | 5.0 |
| 2.95 | ddd | 1H | H-6α | 16.6 | 5.4 | 2.2 |
| 3.11 | ddd | 1H | H-5α | 13.7 | 13.6 | 5.4 |
| 3.55 | s | 3H | OMe-1 | | | |
| 3.86 | s | 3H | OMe-2 | | | |
| 3.87 | s | 3H | OMe-3 | | | |
| 4.00 | s | 3H | OMe-10 | | | |
| 6.54 | s | 1H | H-4 | | | |
| 6.85 | d | 1H | H-11 | 10.7 | | |
| 7.12 | s | 1H | H-8 | | | |
| 7.24 | d | 1H | H-12 | 10.7 | | |

¹³C-NMR (300 MHz, $CDCl_3$): 29.27 ppm (C-5)-43.33 (C-6)-55.96 (OMe-10)-56.44 (OMe-3)-61.07 (OMe-2)-61.12 (OMe-1)-106.96 (C-4)-112.40 (C-11)-124.50 (C-12b)-132.00 (C-4a)-132.80 (C-8)-135.30 (C-12)-136.15 (C-12a)-141.80 (C-2)-150.16 (C-1)-151.83 (C-7a)-153.70 (C-3)-164.10 (C-10)-179.40 (C-9)-205.60 (C-7).

Example 3

Preparation of the Condensation Product between Thiocolchicine and 3,5-ditert-butyl-1,2-benzoquinone (IIa: R=SMe; R₁=Me)

500 mg of deacetylthiocolchicine (M.W. 373, 1.34 mmol) and 590 mg of 3,5-di-tert-butyl-1,2-benzoquinone (M.W. 220, 2.69 mmol) are dissolved in 50 ml of methanol, under normal atmosphere.

The reaction is followed by TLC ($CH_2Cl_2$:acetone 30:1) and after about 18 hours the solvent is evaporated off under vacuum.

The warm crude is dissolved in 1 volume of ethyl acetate, 1–1.5 volumes of hexane are added and the mixture is cooled on ice. The reaction product is recovered by filtration, the yield being 70%. This compound has the following chemical-physical and spectroscopical characteristics.

M.p. 238° C. with decomposition MS (E.I.): 573 m/z (33%)-558 (1%)-545 (100%)-530 (9%)-514 (7%)-314 (4%)-301 (4%)-265 (7%)-249 (7%). $^1$H-NMR (300 MHz, CDCl$_3$).

| ppm | molt | int | type | J(Hz) | J(Hz) |
|------|------|-----|------|-------|-------|
| 1.30 | s    | 9H  | tBu  |       |       |
| 1.40 | s    | 9H  | tBu  |       |       |
| 2.45 | s    | 3H  | SMe  |       |       |
| 3.05 | dd   | 1H  | H-5  | 14.0  | 4.0   |
| 3.30 | dd   | 1H  | H-5  | 14.0  | 4.0   |
| 3.55 | s    | 3H  | OMe  |       |       |
| 3.83 | s    | 3H  | OMe  |       |       |
| 3.87 | s    | 3H  | OMe  |       |       |
| 3.86 | t    | 1H  | H-6  | 4.0   |       |
| 6.65 | s    | 1H  | H-4  |       |       |
| 7.08 | d    | 1H  | H-11 | 11.0  |       |
| 7.20 | d    | 1H  | H-5' | 2.0   |       |
| 7.26 | d    | 1H  | H-3' | 2.0   |       |
| 7.28 | d    | 1H  | H-12 | 11.0  |       |
| 7.33 | s    | 1H  | H-8  |       |       |

$^{13}$C-NMR (300 MHz, CDCl$_3$): 15.71 ppm (SMe)-30.33 (C(CH$_3$)$_3$)-31.95 (C(CH$_3$)$_3$)-34.96 ((C(CH$_3$)$_3$)-35.25 (C(CH$_3$)$_3$)-36.60 (C-5)-56.41 (OMe-3)-61.81 (OMe-1)-61.64 (OMe-2)-76.47 (C-6)-109.80 (C-4)-123.56 (C-5')-124.61 (C-3')-125.75 (C-12b)-126.80 (C-11)-132.28 (C-4')-133.58 (C-6')-135.13 (C-8)-135.47 (C-4a)-136.10 (C-12)-137.01-(C-12a)-142.35 (C-2)-143.21 (C-7a)-144.88 (C-2')-147.19 (C-1')-152.06 (C-1)-153.78 (C-3)-159.85 (C-10)-164.68 (C-7)-182.26 (C-9).

Example 4

Preparation of tablets containing compound (Ia)

| | |
|---|---|
| Compound Ia | 25 mg |
| Lactose | 47 mg |
| Microcrystalline cellulose | 20 mg |
| Cross-linked sodium carboxymethyl cellulose | 5 mg |
| Colloidal silica | 1 mg |
| Talc | 1 mg |
| Magnesium stearate | 1 mg |

Example 5

Preparation of a liposome cream containing compound (IIa)

| | |
|---|---|
| Compound IIa | 0.20 g |
| Phosphatidylcholine | 20.00 g |
| Cholesterol | 0.50 g |
| Butylhydroxytoluene | 0.01 g |
| 95% Ethanol | 8.00 g |
| Disodium edetate | 0.15 g |
| Imidazolidinyl urea | 0.30 g |
| Sodium dehydroacetate | 0.20 g |
| Hydroxyethyl cellulose (Natrosol 250 HHX-Aqualon) | 2.00 g |
| Distilled water | 67.75 |

Example 6

Preparation of an injectable solution containing compound (Ia)

| | |
|---|---|
| Compound Ia | 15 mg |
| PEG-660 12-hydroxystearate | 2.500 mg |
| Propylene glycol | 1.000 mg |
| alcohol q.s. to | 5 ml |

What is claimed is:

1. A compound of formula I:

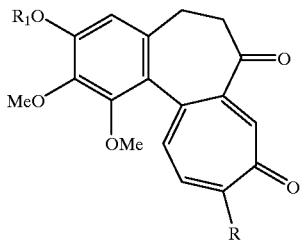

(I)

wherein R is methoxy or methylthio; and R$_1$ is a straight chain or branched alkyl group having 1 to 6 carbon atoms, a straight chain or branched alkenyl group having 1 to 6 carbon atoms, a cyclic aliphatic moiety, a heterocyclic moiety, a saturated or unsaturated monocarboxylic acyl residue, a saturated or unsaturated dicarboxylic acyl residue, a saturated or unsaturated amino acid acyl residue, a β-D-glucose residue, or a 6-deoxylgalactose residue, with the proviso that, when R is methoxy, R$_1$ is other than methyl or acetyl.

2. The compound of claim 1 wherein R is methoxy.
3. The compound of claim 1 wherein R is methylthio.
4. The compound of claim 3 wherein R$_1$ is methyl.
5. The compound of formula II:

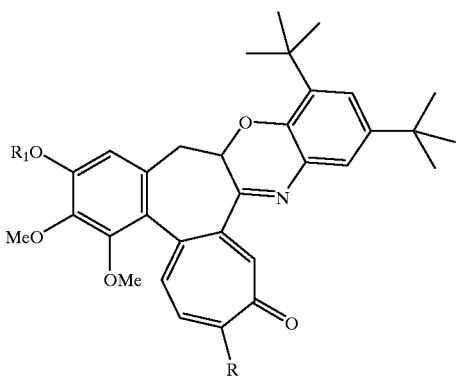

(II)

wherein R is methoxy or methylthio; and R$_1$ is a straight chain or branched alkyl group having 1 to 6 carbon atoms, a straight chain or branched alkenyl group having 1 to 6 carbon atoms, a cyclic aliphatic moiety, a heterocyclic moiety, a saturated or unsaturated monocarboxylic acyl residue, a saturated or unsaturated dicarboxylic acyl residue, a saturated or unsaturated amino acid acyl residue, a β-D-glucose residue, or a 6-deoxylgalactose residue.

6. The compound of claim 5 wherein R is methoxy.
7. The compound of claim 5 wherein R is methylthio.

8. The compound of claim 6 wherein $R_1$ is methyl.

9. The compound of claim 7 wherein $R_1$ is methyl.

10. A pharmaceutical composition suitable for administration to a patient comprising a pharmaceutically effective amount of the compound of claim 1 and an excipient.

11. A pharmaceutical composition suitable for administration to a patient comprising a pharmaceutically effective amount of the compound of claim 5 and an excipient.

12. A method of preparing a compound of formula I:

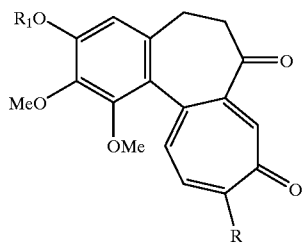

(I)

wherein R is methoxy or methylthio; and $R_1$ is a straight chain or branched alkyl group having 1 to 6 carbon atoms, a straight chain or branched alkenyl group having 1 to 6 carbon atoms, a cyclic aliphatic moiety, a heterocyclic moiety, a saturated or unsaturated monocarboxylic acyl residue, a saturated or unsaturated dicarboxylic acyl residue, a saturated or unsaturated amino acid acyl residue, a β-D-glucose residue, or a 6-deoxylgalactose residue, with the proviso that, when R is methoxy, $R_1$ is other than methyl or acetyl; comprising:

selecting a first compound from the group consisting of N-deacetylcolchicine and N-deacetylthiocolchicine; and reacting said first compound with 4-formyl-1-methylpyridinium p-toluenesulfonate and 1,8-diazabicyclo[5.4.0]undec-7-ene at a temperature and for a time sufficient to form the compound of formula I.

13. A method of preparing a compound of formula II:

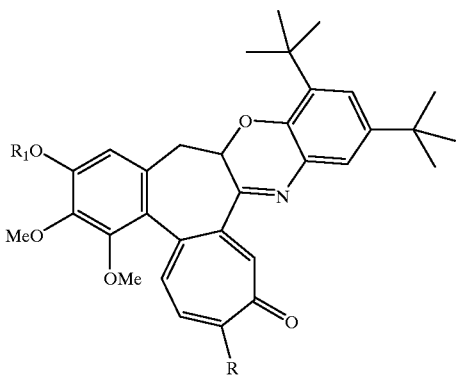

(II)

wherein R is methoxy or methylthio; and $R_1$ is a straight chain or branched alkyl group having 1 to 6 carbon atoms, a straight chain or branched alkenyl group having 1 to 6 carbon atoms, a cyclic aliphatic moiety, a heterocyclic moiety, a saturated or unsaturated monocarboxylic acyl residue, a saturated or unsaturated dicarboxylic acyl residue, a saturated or unsaturated amino acid acyl residue, a β-D-glucose residue, or a 6-deoxylgalactose residue; comprising:

selecting a first compound from the group consisting of N-deacetylcolchicine and N-deacetylthiocolchicine; and reacting said first compound with 3,5-ditert-buty-1,2-benzoquinone at a temperature and for a time sufficient to form the compound of formula II.

* * * * *